United States Patent [19]
Bowman et al.

[11] Patent Number: 5,279,317
[45] Date of Patent: Jan. 18, 1994

[54] ENDOSCOPIC CANNULATED INSTRUMENT FLUSHING APPARATUS FOR FORCING A CLEANING SOLUTION THROUGH AN ENDOSCOPIC CANNULATED INSTRUMENT FOR REMOVAL OF GROSS DEBRIS

[76] Inventors: Michael D. Bowman, 1527 Romany Ct., Olathe, Kans. 66061; Michael J. Armentrout, 2757 W. 131st St., Leawood, Kans. 66209; Drake L. Koch, 3309 Genessee, Kansas City, Mo. 64111

[21] Appl. No.: 47,119
[22] Filed: Apr. 14, 1993

Related U.S. Application Data
[63] Continuation-in-part of Ser. No. 22,994, Feb. 26, 1993.
[51] Int. Cl.$^5$ .............................................. B08B 3/04
[52] U.S. Cl. ........................... 134/166 C; 134/169 C; 134/201; 134/170
[58] Field of Search .......................... 134/135, 155, 166 C, 169 C, 170, 182, 183, 154, 174, 186, 201; 68/223

[56] References Cited

U.S. PATENT DOCUMENTS

| | | | |
|---|---|---|---|
| 1,817,759 | 8/1931 | O'Connor | 68/223 |
| 2,221,892 | 8/1940 | Giese | 134/170 |
| 3,096,776 | 7/1963 | DeWitt | 134/183 |
| 3,101,089 | 8/1963 | Brown et al. | 134/186 |
| 3,459,202 | 8/1969 | Roberson | 134/155 X |
| 3,555,990 | 1/1971 | Dittman et al. | 134/186 |
| 3,904,431 | 9/1975 | Dinerman | 134/182 |
| 4,198,153 | 4/1980 | Namlin | 134/186 X |
| 4,281,646 | 8/1981 | Kinoshita | 128/6 |
| 4,288,882 | 9/1981 | Takeuchi | 15/88 |
| 4,439,884 | 4/1984 | Glorni | 15/104.92 |
| 4,525,220 | 6/1985 | Sasa et al. | 134/21 |
| 4,667,691 | 5/1987 | Sasa | 134/169 C |
| 4,748,007 | 5/1988 | Gaudion et al. | 134/170 X |
| 5,090,433 | 2/1992 | Kamaga | 134/169 C |
| 5,201,331 | 4/1993 | Tapper | 134/170 |

FOREIGN PATENT DOCUMENTS
280168 9/1970 U.S.S.R. .............................. 134/196 C

Primary Examiner—Frankie L. Stinson
Attorney, Agent, or Firm—Kenneth W. Iles

[57] ABSTRACT

An endoscopic instrument cleaning apparatus includes a syringe coupled to a flushing chamber by a form-fitting stopper. A distal, or instrument receiving end of the flushing chamber is inserted into a supply of cleaning fluid and the plunger of the syringe is drawn out to its fully retracted length, thereby filling the syringe and the flushing chamber with cleaning fluid. Then the distal end of an endoscopic instrument is inserted about through an aperture in a stopper having the shape of a conical frustum and is inserted into the flushing chamber to a depth of about 4 inches (10 cm) and the plunger of the syringe is thrust forward to inject pressurized cleaning solution through the endoscopic instrument. In another embodiment, the syringe receiving stopper is recessed within a proximal end of the flush chamber by about ⅜ inches (0.95–1.00 cm) and a tightly fitting tubular insert is glued into the recess to eliminate the possibility that the syringe receiving stopper will be blown out of the flushing chamber by fluid pressure when it is used. Alternatively, an inward projecting lip is formed in the distal end of the flush chamber for the same purpose. A rectangular flushing board includes a neck having a pair of aligned yokes for seating and holding the syringe body to eliminate wrist and thumb strain. In another embodiment, a flushing chamber is formed as an extension to the body of a syringe, thereby eliminating the need for a separate flushing chamber.

10 Claims, 8 Drawing Sheets

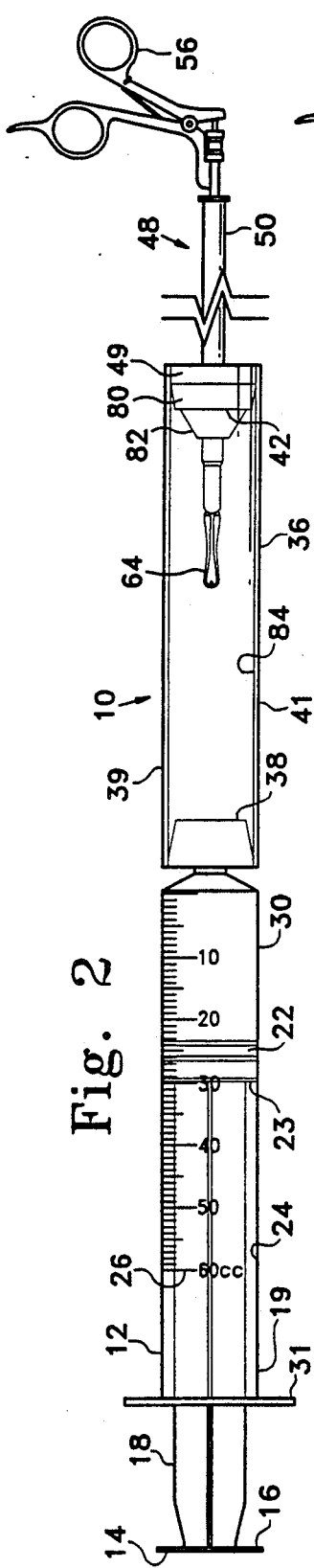
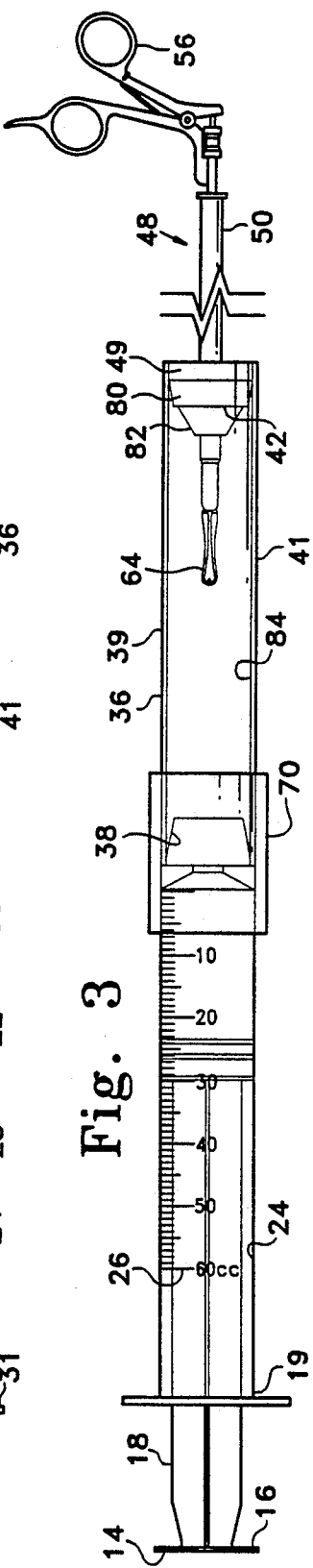
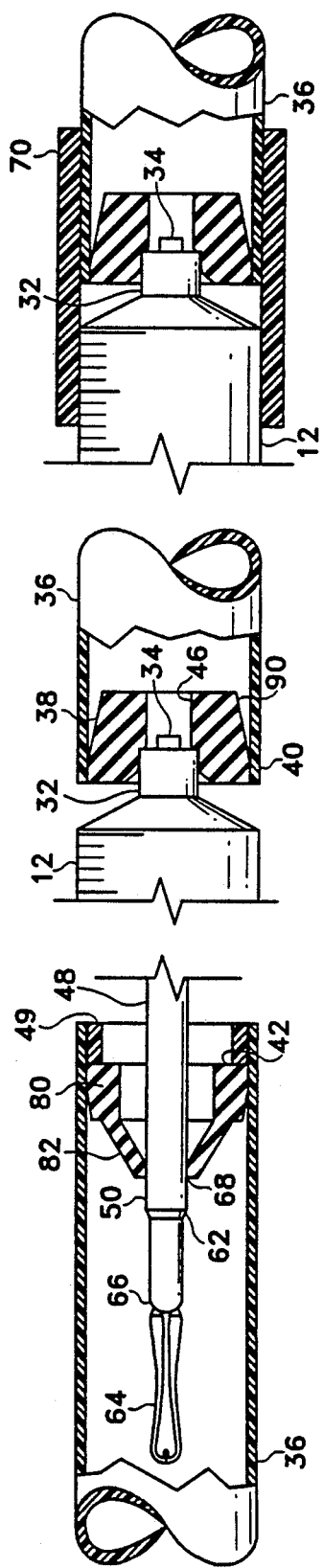

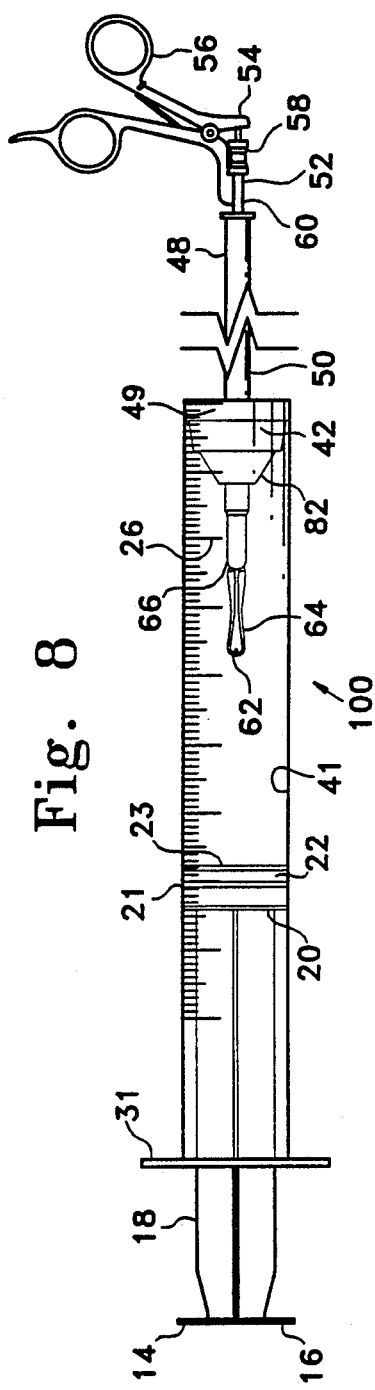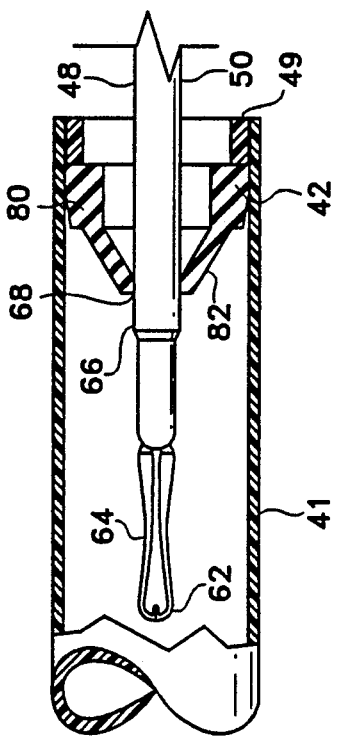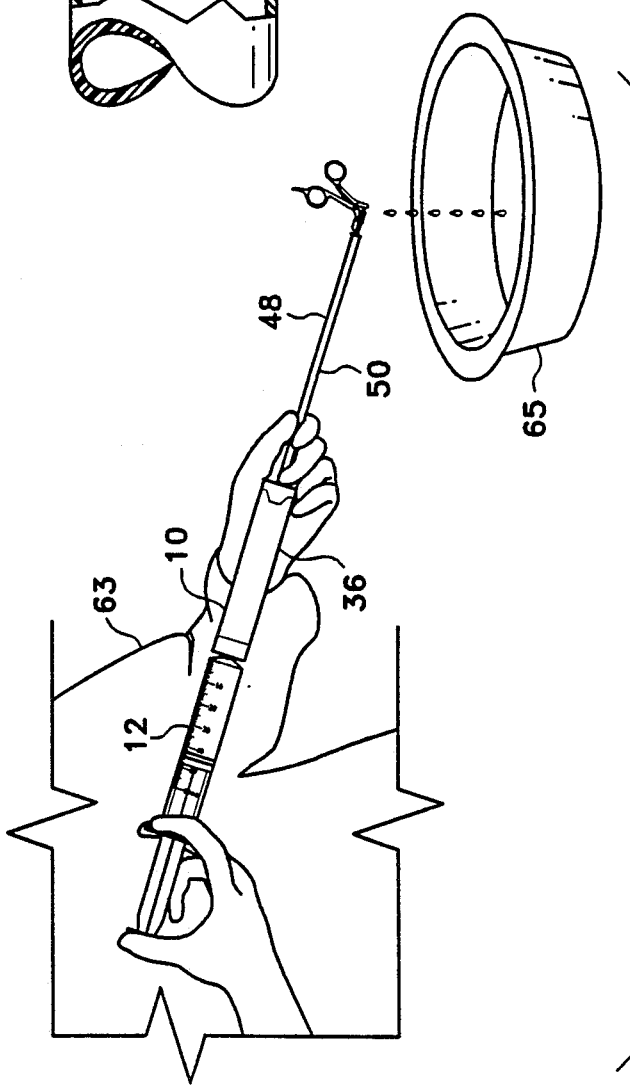

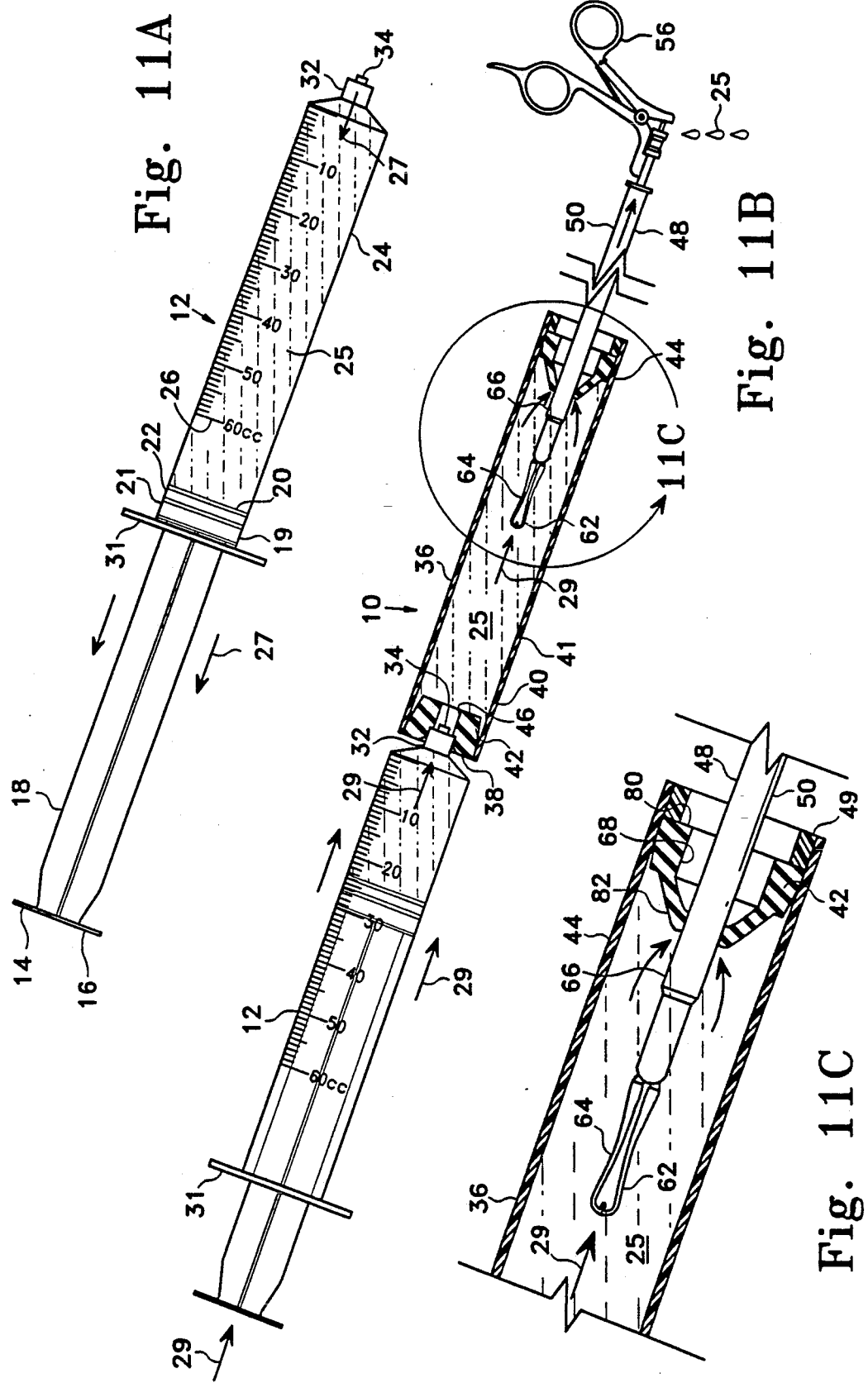

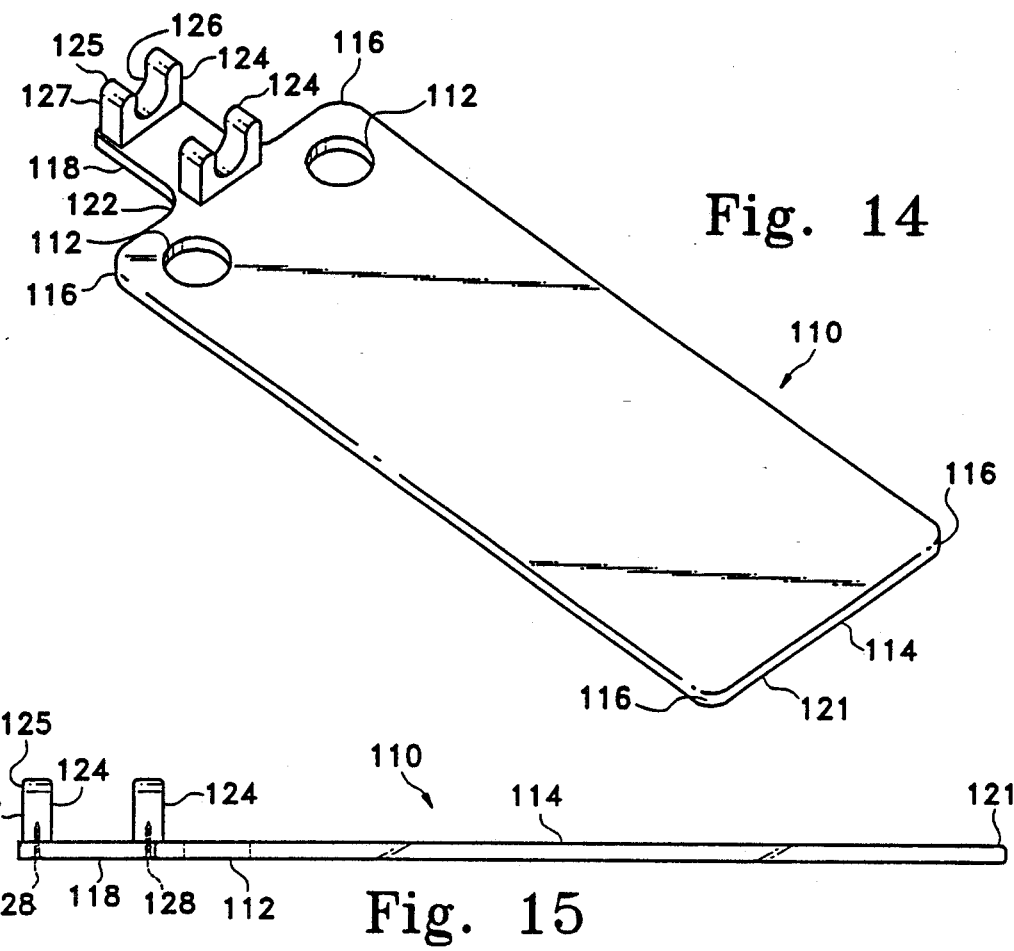
Fig. 14
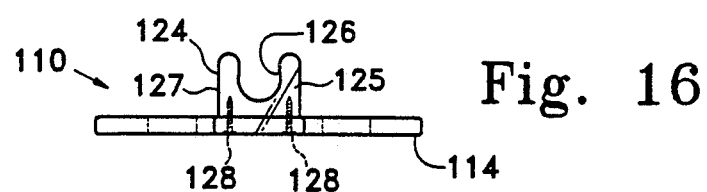
Fig. 15
Fig. 16
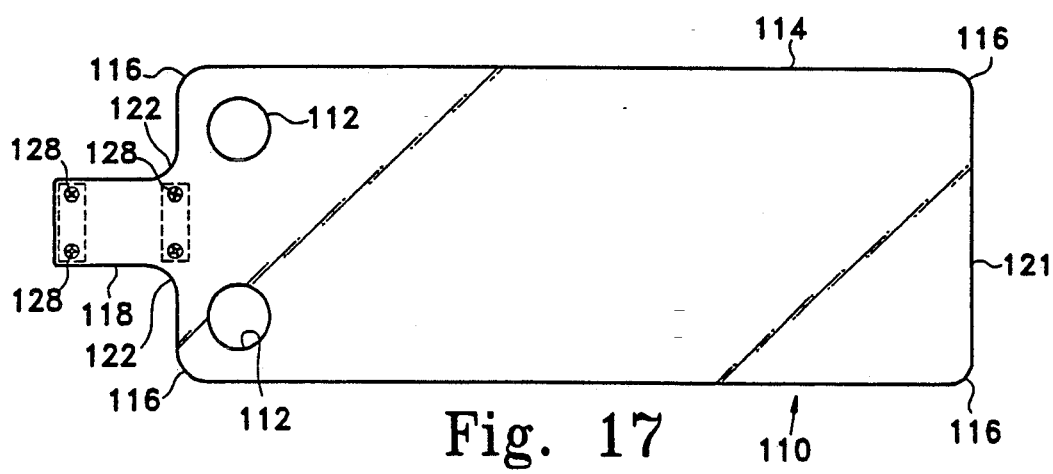
Fig. 17

ENDOSCOPIC CANNULATED INSTRUMENT FLUSHING APPARATUS FOR FORCING A CLEANING SOLUTION THROUGH AN ENDOSCOPIC CANNULATED INSTRUMENT FOR REMOVAL OF GROSS DEBRIS

CROSS-REFERENCE TO RELATED APPLICATIONS

This Application is a continuation-in-part of U.S. patent application Ser. No. 08/022,994, filed Feb. 26, 1993, now pending.

BACKGROUND OF THE INVENTION

1. Field of the Invention

The present invention is related to an apparatus and process for cleaning endoscopic surgical instruments by flushing the cannula. More particularly, the present invention is directed to a hand-operated apparatus for forcing a cleaning solution through an endoscopic cannulated surgical instrument to remove gross debris from surgery that and utilizes a syringe or other source of pressurized cleaning solution to provide the motive power required for forcing a cleaning solution through the cannula of an endoscopic cannulated instrument.

2. Description of Related Art Including Information Disclosed Under 37 C.F.R. Sections 1.97–1.99.

Increasingly, surgeries are conducted with endoscopic cannulated instruments, or instruments, which are inserted through minimal surgical openings in the body to reduce the invasiveness of surgical procedures. Endoscopic instruments are long instruments having a narrow elongated sleeve or housing with cables, rods and the like being threaded through them and connected to tools on the working, or distal, end that are manipulated by squeezing scissors-like handles, or other control mechanism, on the other, proximal end, which remains outside the patient. Many endoscopic instruments have a rigid outer housing and a rod reciprocates inside the housing to actuate a surgical tool on the distal end of the endoscopic instrument. Other endoscopic instruments are flexible and are used primarily in conjunction with a cannulated endoscope. For purposes of this disclosure, an endoscopic instrument includes all instruments used in minimally invasive surgery and having an elongated housing or sleeve that forms a cannula that houses any type of control mechanism, e.g., rod or cable, to control a tool or instrument for use inside a patient's body. The present invention is directed to an apparatus for cleaning gross debris from any such type of medical instrument by flushing the cannula.

All these instruments are cannulated instruments, that is, each has an elongated cannula, which is almost completely filled with instrument and controls. It is the cannula that traps gross debris, which is invariably drawn into the cannula when the control rods, wires, and the like reciprocate within the cannula formed by the outer housing or sleeve of endoscopic instruments.

During use, endoscopic instruments draw bodily fluids and tissues and other matter from the patient, known collectively as "gross debris," into the elongated tubular housing of the endoscopic instrument. These tubes are quite small and most of their volume is filled with the control rod or the like, leaving little room for cleaning. The sleeve or housing of endoscopic instruments are not sealed, and the reciprocal movement of the inner workings within the sleeve invariably draws gross debris into the sleeve, from which it cannot be removed effectively using devices currently known in the medical profession. Further, surgeons operating inside the abdominal cavity pressurize the abdominal cavity with carbon dioxide to separate organs and tissues from one another and this pressurized gas leaks through cannulated instruments, forcing gross debris into the housing of the endoscopic or cannulated instruments.

Because there is virtually no way to disassemble reusable instruments, they tend to trap blood, other fluids, and tissue in the space between the tool control rod and the housing. This gross matter inhibits the ability of pressurized steam, ethylene oxide or chemical sterilants to effectively reach all parts of the instrument. This may allow blood-borne pathogens to survive inside the housing, greatly increasing the risk of patient infection from cross contamination from other patients. Even if it were possible to disassemble cannulated instruments for thorough cleaning, it would be prohibitively expensive and time consuming to do so.

Endoscopic instruments are cleaned and sterilized according to hospital protocol, which varies widely between institutions. In some cases, endoscopic instruments are sterilized during the night. During the day, however, they may be repeatedly used for consecutive surgeries on different patients with minimally accepted cleaning and sterilization practices. With the increase of endoscopic procedures and lack of proper cleaning techniques, gross debris build up is probable and potentially widespread. In the age of AIDS, and contagious hepatitis type B, this situation is obviously of great concern, which has been recognized, but not solved, by the medical community.

Currently about 2.2 million surgical procedures employing endoscopic instrument are performed each year. It is estimated that by the year 2000 more than one-half of all surgeries will performed with minimally invasive techniques, that is, with endoscopic instrument, which will be about 11 million surgeries per year. The potential for serious cross-contamination between patients and resulting transmission of disease is clear, but no clear, effective and affordable solution to the problem is known.

Some approaches to addressing the problem of removing gross debris from the exterior of endoscopes, which are tightly sealed and do not admit debris, as they have no cannula, have led to issued patents, some of which are discussed below. No issued patents specifically directed to removing gross debris from the cannula of endoscopic cannulated instruments, however, have been located.

U.S. Pat. No. 4,667,691, issued to Sasa on May 26, 1987 (Sasa '691), discloses a "Device for Cleaning channels of an Endoscope" comprising syringe provides the power to force a liquid cleaning solution through an endoscope through a complex series of valves and tubing. The fluid flows first through a main body, into which it is drawn from a fluid storage tank and from which it is forced into the tubing, other valves, and the endoscope and so forth.

U.S. Pat. No. 4,525,220, issued to Sasa et al. on Jun. 25, 1985 (Sasa et al. '22), discloses a "Method of Cleaning Endoscope Channels" comprising a number of methods of using the device disclosed and claimed in Sasa '691, which is described above.

U.S. Pat. No. 4,439,884, issued to Giorni on Apr. 3, 1984 (Giorni '884) discloses a "Container with Bristles for Cleaning Instruments" comprising a cylindrical vessel with an open top. A plurality of bristles project horizontally and inwardly from the inside side wall toward the center of the vessel. The vessel is filled with an appropriate cleaning fluid. The instrument is submerged in the fluid and is rotated by hand to clean it. If desired, the instrument may be supported by a ring 9 connected to a clamp 10 on the outside of the vessel.

U.S. Pat. No. 4,288,882, issued to Takeuchi on Sep. 15, 1981 (Takeuchi '882), discloses an "Endoscope Sheath Cleaning Device" comprising a bulky free-standing machine having a J-shaped tube into which an endoscope sheath is inserted progressively and repeatedly, either by hand or machine, while water or other solution is sprayed on it from two opposed nozzles located near the top of the apparatus. The spray from the nozzles is directed downward onto a brush set which brushes the exterior of the sides of the endoscope. It does not appear that any fluid is forced through the endoscope by this apparatus.

U.S. Pat. No. 4,281,646, issued to Kinoshita on Aug. 4, 1981 (Kinoshita '646), comprises a window washer for cleaning the observation window at the end of an endoscope having an observation window, while the endoscope is in use.

None of these devices is directed to removing gross debris from the cannula of endoscopic cannulated surgical instruments in general. Moreover, none of these devices offers an inexpensive, disposable and reliable endoscopic cannulated instrument cleaning apparatus for removing gross debris from the cannula that is also simple, convenient and easy to use and to manufacture. Therefore, a serious need exists for an endoscopic cannulated instrument cleaning apparatus that is inexpensive, disposable and reliable, while also being simple, convenient and easy to use and to manufacture. Such an apparatus is disclosed and claimed in this document, as follows.

SUMMARY OF THE INVENTION

Accordingly, it is a primary object of the present invention to provide an endoscopic cannulated instrument cleaning apparatus capable of flushing gross debris from an endoscopic cannulated instrument.

It is another object of the present invention to provide an endoscopic cannulated instrument cleaning apparatus that is simple, convenient and easy to use.

It is another object of the present invention to provide an endoscopic cannulated instrument cleaning apparatus that is inexpensive, simple, convenient and easy to manufacture.

It is another object of the present invention to provide an endoscopic cannulated instrument cleaning apparatus that is disposable.

An endoscopic cannulated instrument cleaning apparatus according to the present invention is a flushing device designed to help clear cannulated instruments of gross material as part of the cleaning process. Preferably, it is for single patient use and is disposable. The endoscopic cannulated instrument cleaning apparatus is manufactured in sizes that fit most cannulated instruments. Regular use of the endoscopic cannulated instrument cleaning apparatus helps extend the life of expensive cannulated surgical instruments and reduces the risk of patient infection from cross contamination.

In use, it is important to follow all hospital and other indicated protocol for cleaning and processing instruments. In a preferred embodiment, a 60 cc syringe is connected to a flushing chamber. Then the distal end of the endoscopic instruments cleaning apparatus is submerged into a flushing solution and the syringe plunger is retracted to fill the flush chamber with flushing solution. Next, the worker opens or disassembles all necessary exit ports on a cannulated instrument having flush ports to allow a free flow of the flushing solution. Then the distal end of the endoscopic or cannulated surgical instrument is inserted into the flush chamber a sufficient distance to insure that the distal end of the housing is within the flush chamber. To flush gross material from the endoscopic or cannulated instrument, depress the syringe plunger until a desired amount of flushing solution enters and exits the instrument. The present invention is an aid to the over-all cleaning process and is not intended to replace other elements of hospital protocol. Currently used hospital protocols, however, do not remove gross debris from the cannula of these instruments. Consequently, although the instruments may be thoroughly sterilized, organic matter trapped inside the cannula provides a prime culture medium for bacteria growth. And, of course, if the instrument is not thoroughly sterilized, bacteria or viruses may survive inside the cannula, where it may have a good culture medium. Such debris, bacteria, and virus may be introduced into another patient during a later-performed surgery.

In the preferred embodiment described herein, a syringe is used to provide the force necessary for flushing the cannula of an endoscopic cannulated instrument with a cleaning or flushing solution. This source of pressurized cleaning solution has been selected because it is inexpensive, disposal, and readily available at any hospital. Other sources of pressurized flowing cleaning, or flushing, solution could easily be used, including, for example, hand or foot operated pumps, electrical pumps, and the like. These are more expensive and more difficult to obtain, especially in the instrument cleaning and sterilizing departments of hospitals, which typically have only small budgets.

When a syringe is used to provide a source of pressurized flushing solution, it has been found that some workers experience soreness in the wrist and thumb when using the present invention to flush several or many endoscopic cannulated surgical instruments. This minor difficultly has been overcome by providing a flushing board having a pair of yokes fixed to a neck of the flushing board by stainless steel screws, with each yoke including a U-shaped channel sized to readily hold the cylindrical body of a syringe. The handle portion of the syringe is placed on the outside or upper side of a proximal yoke. The handle is wider than the U-shaped channel in the yoke, so the yoke holds the syringe in place, allowing the worker to press against the syringe plunger with his palm while keeping her wrist straight. This has completely eliminated the need to use the thumb and has completely eliminated user fatigue and soreness.

Other objects and advantages of the present invention will become apparent from the following description taken in connection with the accompanying drawings, wherein is set forth by way of illustration and example, the preferred embodiment of the present invention and the best mode currently known to the inventors for carrying out their invention.

BRIEF DESCRIPTION OF THE DRAWINGS

FIG. 2 is a side elevation of the endoscopic cannulated instrument flushing apparatus of FIG. 1 shown with the plunger of the syringe in a position preparatory to the cleaning stroke.

FIG. 3 is a side elevation of the endoscopic cannulated instrument flushing apparatus of FIG. 1 shown with a bracing sleeve for reenforcing the connection between the syringe and the flush chamber.

FIG. 4 is an enlarged cross sectional elevation of the endoscopic instrument flushing apparatus of FIG. 1 showing the instrument cleaning end of the endoscopic instrument cleaning apparatus with an instrument in place.

FIG. 5 is an enlarged cross sectional elevation of the endoscopic cannulated instrument flushing apparatus of FIG. 1 showing the syringe accepting end of the endoscopic instrument flushing apparatus.

FIG. 6 is an enlarged cross sectional elevation of the endoscopic cannulated instrument flushing apparatus of FIG. 3 showing the syringe accepting end of the present invention, and the bracing sleeve about the ends of the syringe and the tubular flushing chamber, where the two respective parts mate.

FIG. 8 is a side elevation of the endoscopic cannulated instrument flushing apparatus of FIG. 7.

FIG. 9 is an enlarged cross sectional view of a the instrument accepting end of the endoscopic cannulated instrument flushing apparatus of FIGS. 1 and 7.

FIG. 10 is an environmental perspective view of the endoscopic cannulated instrument flushing apparatus of FIG. 1 shown in use by a medical worker to clean an endoscopic cannulated instrument, wherein the operation of both embodiments (i.e., of FIGS. 1, 7) is the same.

FIG. 11A is a side elevation of a syringe that forms a portion of the endoscopic cannulated instrument cleaning apparatus according to the present invention, showing the plunger of the syringe drawn outward preparatory to it maximum stroke.

FIG. 11B is a side elevation, partially in cross section, of an endoscopic cannulated instrument flushing apparatus according to the present invention showing the syringe in about mid-stroke during cleaning of an instrument and illustrating the effect of the fluid flow on the instrument retaining stopper.

FIG. 11C is an enlarged fragmentary cross sectional view of the instrument receiving portion of the endoscopic cannulated instrument flushing apparatus of FIG. 11B, enlarged from the circled "FIG. 11C" portion of FIG. 11B.

FIG. 14 is a perspective view of an endoscopic cannulated instrument flushing apparatus comprising a flushing board according to the present invention for holding an endoscopic cannulated instrument flushing apparatus and instrument during flushing.

FIG. 15 is a front elevation of the apparatus of FIG. 14.

FIG. 16 is a left-side (as shown in FIG. 14) elevation of the apparatus of FIG. 14.

FIG. 17 is a bottom elevation of the apparatus of FIG. 14.

DETAILED DESCRIPTION OF THE PREFERRED EMBODIMENTS

As required by the Patent Statutes and the case law, the preferred embodiment of the present invention and the best mode currently known to the inventors for carrying out the invention are disclosed in detail herein. The embodiments disclosed herein, however, are merely illustrative of the invention, which may be embodied in various forms. Therefore, specific structural and functional details disclosed herein are not to be interpreted as limiting, but merely to provide the proper basis for the claims and as a representative basis for teaching one skilled in the art to which the invention pertains to make and use the apparatus and process disclosed herein as embodied in any appropriately specific and detailed structure.

While the present invention has been described in accordance with the preferred embodiments thereof, the description is for illustration only and should not be construed as limiting the scope of the invention. Various changes and modifications may be made by those skilled in the art without departing from the spirit and scope of the invention as defined by the following claims.

Figure 1:
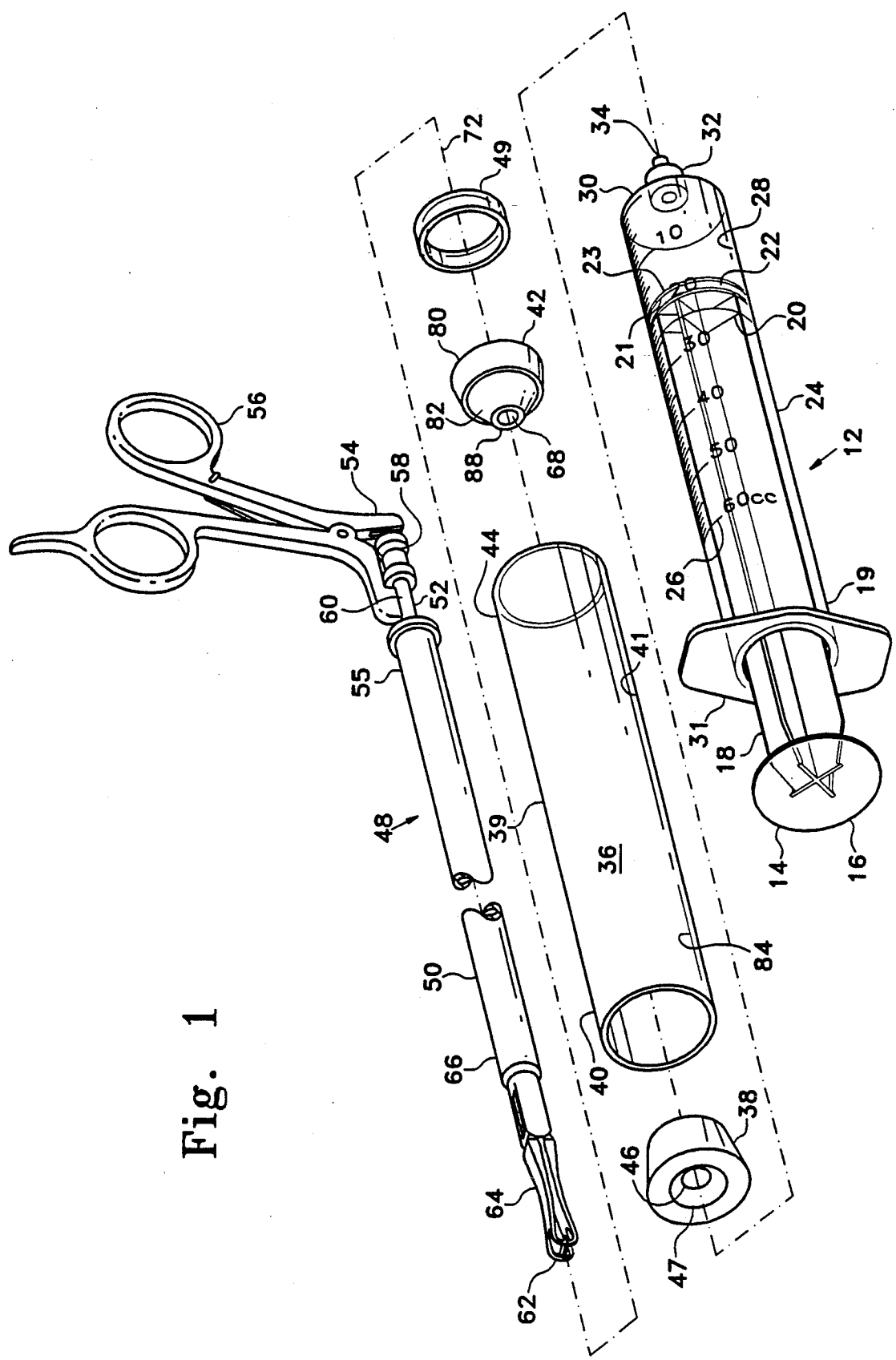
FIG. 1 is an exploded perspective view of one embodiment of an endoscopic cannulated instrument flushing apparatus according to the present invention shown in conjunction with a Babcock tissue grabbing endoscopic instrument for purposes of illustration. The Babcock is shown throughout the drawings as an example of a specific endoscopic instrument being cleaned by the present invention in all embodiments.

Referring now to FIG. 1, there is shown an exploded perspective view of an endoscopic instrument cleaner 10 in conjunction with a Babcock 38 (described below), comprising a syringe 12 having a thumb support 14 integrally formed at a proximal end 16 of a plunger shaft 18 having a distal end 20 fitted with a seal 22. The plunger shaft 18 fits inside a hollow cylindrical body 24, which includes measuring gradation marks 26 and a bifurcated handle portion 31, which allows the body 24 to be placed between the first finger and middle finger with one side of the handle portion 31 resting against the respective two fingers and allowing the user to push the plunger shaft 18 into the body 24 with his thumb. A liquid-tight seal is formed by the seal 22, for example a rubber seal, which bears against the inside wall 28 of the body 24. The plunger shaft 18 is inserted into the body 24 at an open proximal end 19 of the body 24, which accepts the diameter of the circular seal 22, typically an O-ring inserted into a circumferential groove 21 in a head 23 of the plunger shaft 18. The body 24 further includes a distal end 30 having a conical or funnel shape and terminating in a nipple 32. An orifice 34 in the distal end 30 of the body 24 allows fluid communication from the interior of the syringe 12 to an area outside the syringe body 24. The syringe 12 is a conventional disposable syringe, except that in the present invention, no needle is used. In the operation of a conventional syringe, the nipple 32 is immersed into a desired cleaning solution 25 with the plunger shaft 18 pushed into the distal end 30 of the body 24 and then the plunger shaft 18 is drawn away from the distal end 30 (in the direction of the arrows 27 of FIG. 11A) until the desired amount of liquid is drawn into the body 24, as shown in FIG. 11A. Then, when it is desired to expel the liquid from the body 24, the plunger shaft 18 is thrust forward, that is, toward the distal end 30 of the body 24 in the direction of the arrows 29 (FIG. 11B), thereby forcing the cleaning solution 25 in the body 24 through the orifice 34, and therefore through a flush chamber 36. The flush chamber 36 has a body 41 that is preferably cylindrical and is transparent to allow a quick and simple visual confirmation by the worker that the housing 50 of the Babcock 48 is inside the flush chamber 36, allowing the cleaning or flushing solution 25 to enter and exit from the Babcock 48. Because the cleaning solution 25 cannot escape from the apparatus 10, it is forced through the Babcock 48, or other endoscopic instrument, as shown in FIG. 11B. It is important to provide a source of pressurized flowing cleaning, or flushing solution to the flush chamber 36, regardless of the source of that pressurized flowing cleaning solution, for example, a syringe, a manually operated pump, electrical pump, or the like.

Still referring to FIG. 1, a flush chamber 36 comprises a transparent acrylic tube or body 41 having a syringe receiving stopper 38 in a proximal end 40 and an endoscopic instrument receiving stopper 42 in a distal end 44 of the flush chamber 36. The nipple 32 of the syringe 12 is inserted into an aperture 46 in syringe receiving stopper 38, where it is held tight by frictional engagement. An instrument receiving stopper 42 is tightly inserted into the distal end 44 of the flush chamber 36. It has been found that in certain applications, the stopper 42 may be blown out of the flush chamber 36 and it may not be possible to prevent this with conventional adhesives because the flush chamber 36 swells under pressure. This difficulty is easily overcome by inserting the instrument receiving stopper 42 into the flush chamber 36 to create a recess of ¼-⅜ inches (0.635-1.00 cm) at the distal end 44 of the flush chamber 36 and inserting into that recess a tight-fitting sleeve 49 made of the same material as the flush chamber body and binding these two pieces with an organic adhesive that welds the two pieces together. Further, a dye may be added to the adhesive prior to bonding the two pieces together so that the worker can easily see the degree of spreading of the adhesive, with complete coverage of the contact area between the two pieces being desired. In this case frictional engagement as described between the stopper 42, the Babcock 48 and the flush chamber 36 and the reenforcing sleeve insert 49 is sufficient to retain the pieces in their proper spatial relationships without leaks or stopper blow-out at up to 110 pounds per square inch ($7.58 \times 10^2$ dynes/cm$^2$) of pressure. This pressure is far greater than the pressure that can be generated by a hand-operated syringe 12 and is far greater than is required to flush gross debris from an endoscopic instrument.

Figure 13:
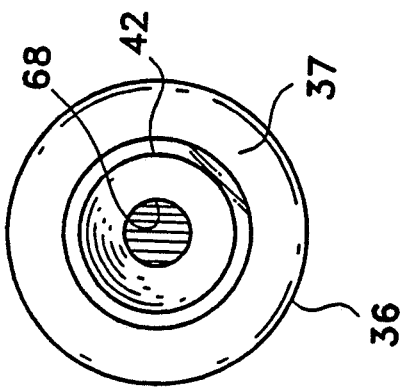
FIG. 13 is a simplified right end elevation of the device of FIG. 2, shown without an instrument inserted therein.
Figure 12:
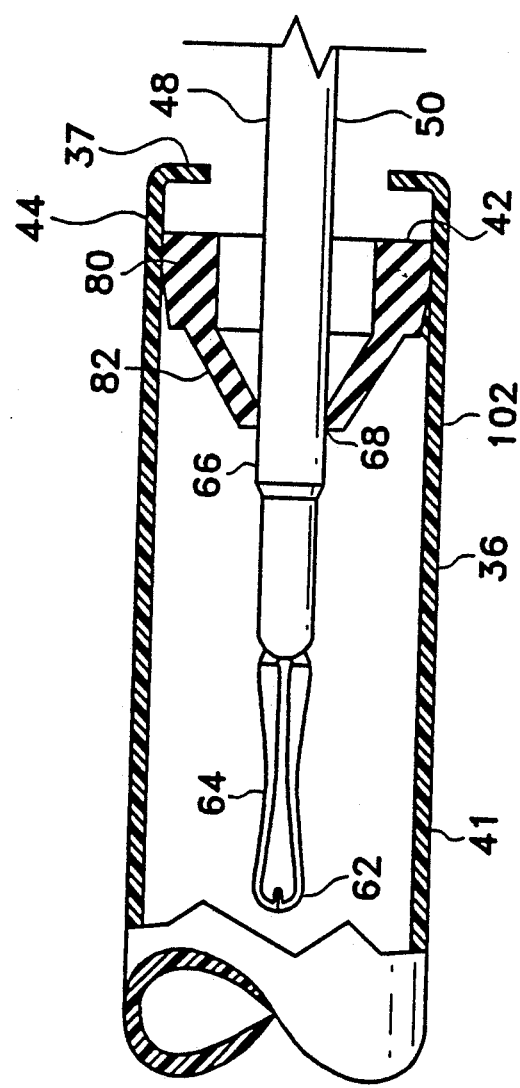
FIG. 12 is an enlarged fragmentary view, partially in cross section, of the instrument receiving end of an alternative embodiment of an endoscopic cannulated instrument flushing apparatus according to the present invention.

Referring now to FIG. 12, there is shown an alternative embodiment of the flush chamber 36 that utilizes a different structure to address the potential problem of the stopper 42 out of the end of the flush chamber 36. In this alternative embodiment, the distal end 44 of the flush chamber 36 is bent inward uniformly about the circumference or perimeter of the flush chamber 36 to form an inwardly projecting circumferential lip 37 that prevents removal of the stopper 42 through the distal end 44. In the best mode currently known to the inventors for carrying out this formation, the stopper 42 is inserted into the distal end 44 of the flush chamber 36 as shown in the figures. Then the distal end 44 is immersed briefly in hot water, making the flush chamber plastic. The distal end 44 is then pressed downwardly onto a mold having a suitable conical frustum shape, which forms the lip 37. The structure of the lip 37 to prevent blowout of the stopper 42 can naturally be used either with the flush chamber 36 or the flush chamber 102, which is an extension of a syringe hollow cylindrical body 24 (FIG. 7) and the technique for forming the lip 37 may be the same in either case. FIG. 13 provides an end plan view taken from the right-hand side of FIG. 12 and showing the flush chamber without an instrument 48 inserted. FIGS. 12 and 13 make it clear that the lip 37 does not cover the opening of the stopper 42, and therefore does not obscure access to the aperture 68 for receiving the Babcock 48 or other instrument to be flushed.

Referring again to FIG. 1, a Babcock 48 includes an external tubular housing 50, through which instrument control rods 52 are routed. The Babcock 48 includes a proximal end 54 having scissors-like handles 56, which are maintained in a normally closed position by a compression spring 58 mounted about a shaft 60, and a distal end 62 which includes a pair of jaws 64. A Babcock is used for gripping and retracting tissues within the patient's body while working with a minimal incision through which the Babcock 48 is inserted. The distal end 62 of the Babcock 48 is inserted through an aperture 68 in the instrument receiving stopper 42 by a medical worker (FIG. 10). The distal end of the Babcock 48 is inserted into the flush chamber 36 to a depth of about 4-6 inches (10-15 cm), which is sufficient to insure that the distal end 66 of the housing of the Babcock 48 is inside the flush chamber 36. Prior to inserting the Babcock 48 into the flush chamber 36, the syringe 12 and the flush chamber 36 are filled with an appropriate cleaning solution by connecting the syringe 12 to the flush chamber 36, with the plunger shaft 18 of the syringe 12 toward the distal end 30 of the syringe 12, immersing the distal end 44 of the flush chamber 36 into an appropriate cleaning solution, which is then drawn into the endoscopic instrument cleaner 10 by drawing the plunger shaft 18 of the syringe 12 away from the distal end 30 of the syringe. Then the Babcock 48, or other endoscopic instrument, is inserted into and through an aperture 68 in the instrument receiving stopper 42 of the cleaner 10, and the plunger shaft 18 of the syringe 12 is thrust toward the distal end 30 of the syringe 12, forcing the cleaning solution through the tubular housing 50 of the Babcock 48. The cleaning solution is thereby forced through the tubular housing 50 and is expelled at the proximal end 55 of the housing 50 of the Babcock 48, into a suitable drainage basin 65 or the like, as shown in FIG. 10. A Babcock 38 is used here merely to illustrate the use of the endoscopic instrument cleaner 10, which can be conveniently used with any style of endoscopic instrument, including, for example, endoscopes, instruments with rigid external housings, instruments with flexible exterior housings, and so forth.

Referring now to FIG. 2, there is shown a side elevation of the endoscopic instrument cleaner 10 with the Babcock 48 in place for cleaning. It is apparent that the jaws 64 cannot be inserted into the apparatus 10 in any fashion that would allow the plunger head 23 to strike any part of the Babcock 48 or other instrument, because the plunger head 23 cannot enter the flush chamber 36. FIGS. 3 and 6 show the same endoscopic instrument cleaner of FIGS. 1, 2, with the addition of a tubular coupling sleeve 70 made of transparent plastic material that is inserted over the proximal end 40 of the flush chamber 36 prior to inserting the syringe 12 into the flush chamber 36. FIG. 6 provides an enlarged fragmentary view partially in section of the sleeve 70 in place on the endoscopic instrument cleaning apparatus 10. The sleeve 70 fits tightly over the external surface of both the syringe 12 and the flush chamber 36 to reenforce the connection between these two pieces. It has been found that the use of the sleeve 70 provides users of the endoscopic instrument cleaner apparatus 10 with increased confidence in the apparatus, keeps the longitudinal axis 72 of both pieces in alignment, and prevents the syringe receiving stopper 38 from disengaging from the flush chamber 36 under pressure.

FIG. 4 provides an enlarged fragmentary cross sectional view of the instrument receiving stopper 42 illustrating that the stopper 42 is a single piece stopper having a substantially cylindrical base 80 flowing into a conical frustum 82 presenting a circular orifice or aperture 68 that penetrates the entire length of the stopper 42, thereby providing a pathway for insertion of the Babcock 48 jaws 64 and housing 50. The conical frustum shape 82 provides a relatively long line of contact between the Babcock 48 and the stopper 42. Further, the stopper 42 is made of a pliable resilient and elastic material, such as medical grade rubber, and the aperture or bore 68 is deliberately designed to be somewhat smaller than the outside diameter of the instrument housing 50. Therefore, when the instrument housing 50 is inserted through the aperture 42, the instrument housing 50 is gripped very tightly, and, simultaneously, the outer diameter of the cylindrical base 80 of the stopper 42 swells due to insertion of the Babcock 48, causing the stopper 42 to bear against the cylindrical side walls 84, further tightening the stopper 42 in the flush chamber 36. Naturally, the stopper is sized to provide a tight fit into the flush chamber 36 in any case. Further, referring to FIG. 11C, when the plunger 18 of the syringe 12 is thrust toward the distal end 20 of the syringe 12, the cleaning solution inside the syringe body 24 applies pressure to the conical frustum 82, causing the end 88 of the stopper 42 to collapse about the Babcock 48, as shown, further tightening the grip of the stopper 42 on the Babcock 48 and causing the cylindrical base of the stopper 42 to swell tighter against the inside walls 84 of the flush chamber 36. In many uses, the frictional engagement of these members as described in this paragraph is sufficient to prevent blowout of the instrument receiving stopper 42, but as a matter of precaution, the use of the sleeve insert 49 as described above is preferred. In any case, blow-out is not a problem with the syringe receiving stopper 38 because it is relatively much longer than the instrument receiving stopper 42, and therefore has a greater surface area in contact with the flush chamber 36 and, therefore, greater frictional engagement with the flush chamber 36. Naturally, it is possible to provide an instrument receiving stopper that has a longer body, and therefore a greater surface area in contact with the flush chamber 36 and greater frictional engagement, which could prevent blow-out.

FIG. 5 provides an enlarged fragmentary side elevation partially in section illustrating the syringe 12 inserted into the syringe receiving stopper 38 of the flush chamber 36. The stopper 38 has a generally conical frustum body 90 throughout the length of its body and the aperture 46 is cylindrical throughout its length. The aperture 46 is smaller in diameter than is the nipple 32 so that inserting the nipple 32 requires substantial force, which swells the body 90 of the stopper 38 against the inside wall 28 of the body 24, sealing the nipple 32 of the syringe 12 into the stopper 38 and seals the stopper 38 into the flush chamber 36 more firmly. Considerable force is required to force the stopper 38 into the flush chamber 36. The stopper 38 is made from a resilient, elastic flexible material, such as medical grade rubber.

Figure 7:
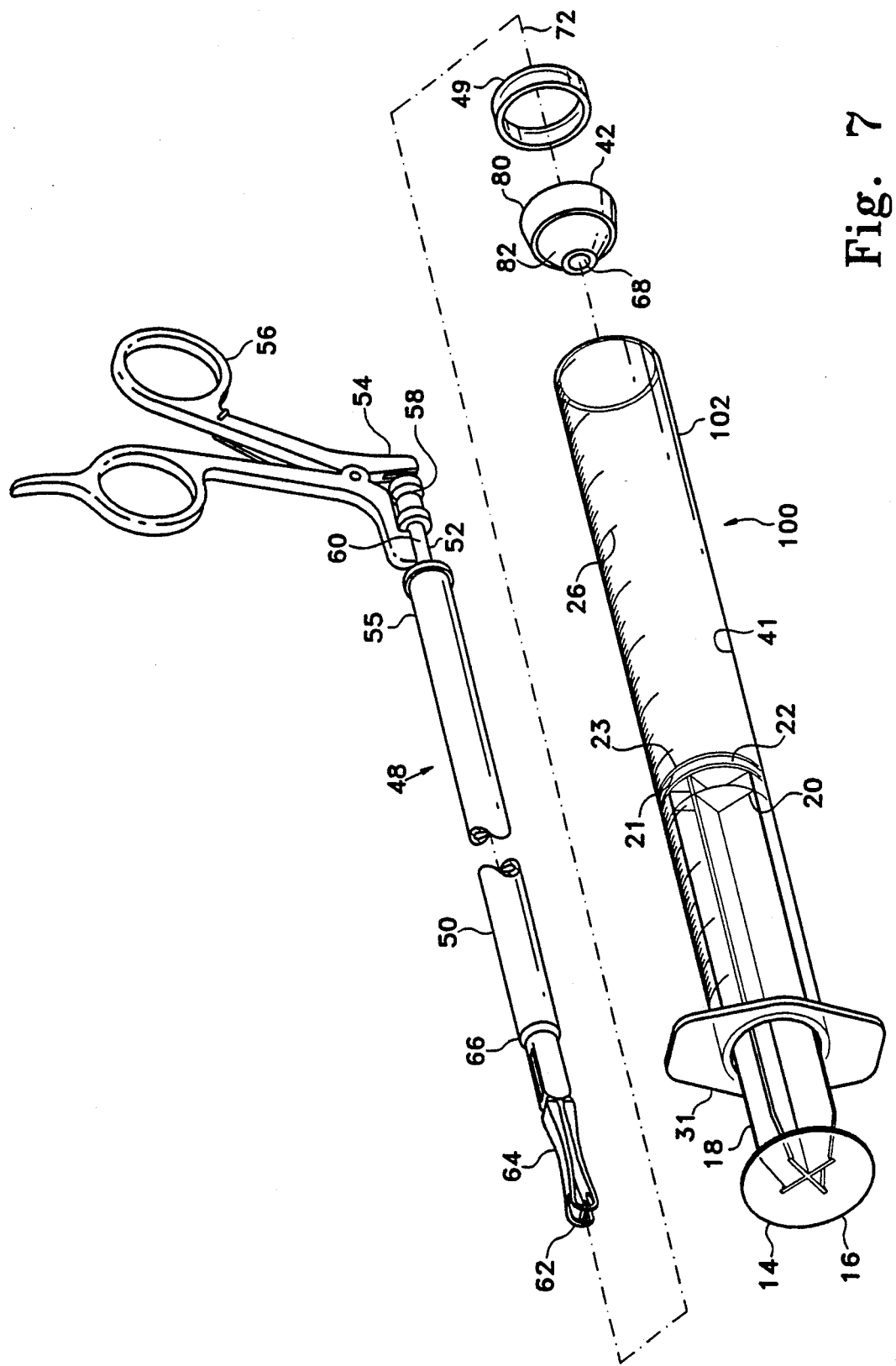
FIG. 7 is an exploded perspective view of an alternative embodiment of an endoscopic cannulated instrument flushing apparatus according to the present invention in which the tubular flushing chamber of the embodiment of FIG. 1 has been built into the body of a syringe.

Referring now to FIG. 7, there is shown an alternative embodiment of an endoscopic instrument cleaning apparatus 100 in which the flush chamber is an extension of the syringe body and, therefore, no syringe receiving stopper is required and no assembly is required prior to use. That is, the flush chamber 36 and the syringe body 24 of FIG. 1 have been combined into a one-piece syringe body and flush chamber 102 in which the flush chamber 102 comprises an elongated body, that is, the flush chamber 102 is longer that the body of a typical syringe relative to the length of the maximum stroke of the plunger shaft 18. The flush chamber 102 and the plunger shaft 18 are of such proportion that the head 23 of the plunger shaft 18 penetrates only a portion of the length of the flush chamber 102 to insure that an endoscopic cannulated instrument can be inserted far enough into the flush chamber 102 for proper cleaning, as described above. The apparatus 100 includes all the conventional syringe 12 components and the instrument receiving stopper 42 and sleeve insert 49 discussed above and so labeled in FIG. 1 and common reference numbers are used for these and other common elements. The apparatus 100 may also include an inwardly projecting circumferential lip 37 about the distal end 44 of the flush chamber 102 (as discussed above and as illustrated in FIGS. 12, 13) as an alternative means to prevent blowout of the stopper 42. Cleaning an endoscopic instrument only requires that the syringe body be filled with cleaning solution and the instrument inserted into the instrument receiving end, and the instrument flushed, as described in greater detail above.

Referring now to FIGS. 14-18 there is shown a flushing board 110 for facilitating use of the endoscopic cannulated surgical cleaning apparatus as discussed to this point. In use it has been found that some workers experience wrist and thumb soreness if they flush many endoscopic cannulated surgical instruments with the present invention in a relatively short period. Further, some difficulty may be experienced in keeping the apparatus and the surgical instrument aligned during flushing. These minor difficulties are overcome by providing additional structure to the invention, namely a flushing board 110. The flushing board 110 includes two grasping holes 112 to make it easier to pick up and carry the flushing board 110. A main body 114 of the flushing board 110 is substantially rectangular with neatly rounded corners 116 in plan view and is relatively thin. The flushing board 110 includes a distal end 121. A neck 118 extends from a proximal end 120 of the flushing board 110 and an opposed pair of neatly rounded corners 122 are located at the juncture of the neck 118 and the main body 114. The neck 118 and the main body 114 are formed from a single sheet of material, which may suitably be a rigid strong plastic material, preferably having a pebble textured nonporous surface for easy cleaning. Alternatively, the flushing board may be made from stainless steel or other material. A pair of yokes 124, each having a central U-shaped channel 126 are fixed to the neck 118 by a plurality of stainless steel screws 128 or other suitable fasteners. The two yokes 124 are spaced apart in parallel relationship along the neck 118 so that their respective U-shaped channels are longitudinally aligned along the neck 118. The centers of the U-shaped channels 126 lie along a longitudinal center line of the flushing board 110. The yokes 124 are made of the same material as the flushing board 110.

Figure 18:
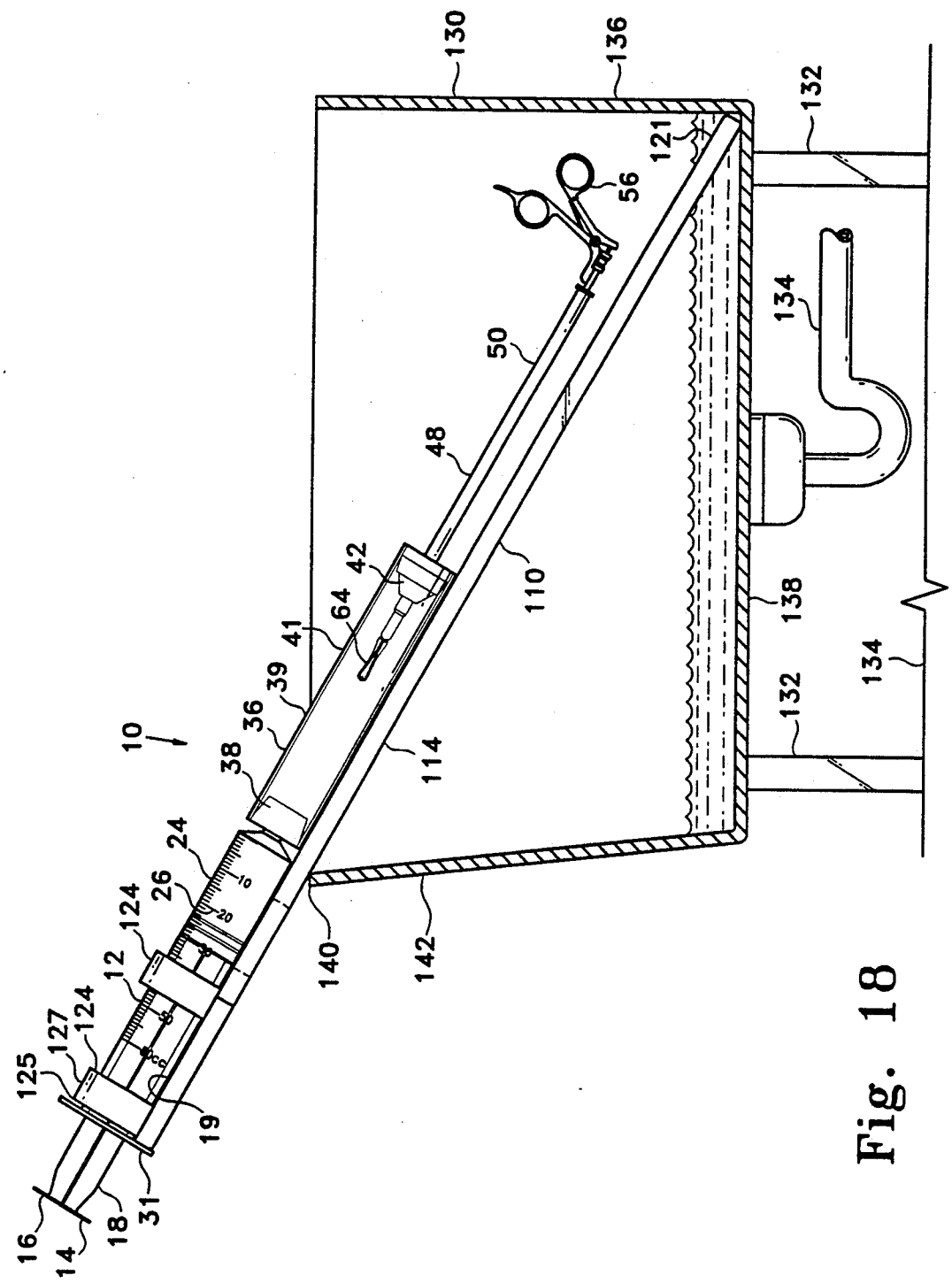
FIG. 18 is a side elevation, partially in cross section, of the endoscopic cannulated cleaning apparatus of the present invention shown in use flushing an instrument in a sink.

Referring now to FIG. 18, there is shown a side elevation, partially in section, of the entire endoscopic cannulated surgical instrument flushing apparatus 10 in use. The flushing board 110 is set into a sink 130 supported by legs 132 standing on a floor 134 and having a suitable drain 134. The distal end 121 is set into the sink 130 against the line joining a side wall 136 and a bottom wall 138 of the sink 130 and the proximal end of the flushing board 110 rests against an upper edge 140 of an opposing side wall 142 of the sink 130. This naturally puts the flushing board 110 on a downward slope with the distal end 121 lower than the proximal end 120 of the flushing board 110.

Still referring to FIG. 18, an apparatus 10 (FIG. 1) or 100 (FIG. 7) is placed on the flushing board 110 with a Babcock 48 inserted for flushing. The syringe body 24 of either embodiment of the apparatus 10, 100 is placed in the two U-shaped channels 126 of the two yokes 124 with the bifurcated handle portion 31 of the syringe body 24 lying against or adjacent to a proximal side 125 of the proximal yoke 127 (see FIGS. 14, 18). The handle portion 31 is wider than the U-shaped channel 126 of either yoke 124, so that the body 24 cannot pass through the yokes 124 when it is placed in the position shown in the drawings and described here.

In use, the worker proceeds as described above, until the actual flushing step. Then the worker places the apparatus 10 or 100, along with the Babcock 48, onto the flushing board as described above. Then the worker merely thrusts the plunger shaft 18 toward the distal end 121 of the flushing board 110 by pressing on the support 14. This can be done with the worker's open palm and allows the worker to utilize the large muscle groups of the arms and chest, reducing strain on the wrist and eliminating strain on the thumb, which need not be used at all. It has been found that this structure enables all workers to flush many endoscopic cannulated surgical instruments without fatigue or soreness.

Other embodiments and forms of the invention may occur to those skilled in the art. For example, it may be possible to mold the flush chamber from a single material, including both the instrument receiving stopper and the syringe receiving stopper, or it may be possible to mold a flush chamber having integral internal collars at each end that can be fitted with grommet-like stoppers that provide suitable seals for the syringe and the endoscopic cannulated surgical instrument to be flushed. In another example, the hand-operated syringe, which provides the force for flushing the endoscopic cannulated surgical instrument, may be replaced by a suitable manual or electrical pump used in conjunction with a plurality of different flushing solutions, with each separate flushing solution having a different purpose. Manual pumps may be operated by a handle or foot treadle. Such an arrangement may be expected to reduce the labor costs associated with cleaning such instruments and would standardize the volume of flushing solution used and the pressure and force used during flushing, which could be expected to lead to more uniform results between different institutions and different operators. Further, it may, for example, be desirable to add a reenforcement sleeve to the instrument receiving end of the flush chamber to hold the endoscopic cannulated instrument in longitudinal alignment with the flush chamber without the necessity of holding the instrument by one hand, which will allow a worker to operate the syringe of the preferred embodiment with two hands, and so on. Therefore, while certain forms of the invention have been illustrated and described, the invention is not limited to those embodiments, except insofar as the limitations are included in the following claims.

We claim:

1. An endoscopic cannulated surgical instrument cleaning apparatus comprising a flush chamber having proximal end and a distal end, flexible, resilient means for sealing said proximal end relative to a source of pressurized flowing solution, said flexible, resilient distal end sealing means further comprising an aperture for receiving and retaining a source of pressurized flow solution by frictional engagement and flexible, resilient means for sealing said distal end relative to an endoscopic cannulated surgical instrument to be flushed, said flexible, resilient distal end sealing means further comprising an aperture for receiving and retaining an endoscopic cannulated surgical instrument by frictional engagement.

2. An apparatus according to claim 1 wherein said distal end sealing means further comprises an inwardly projecting circumferential lip at said distal end of said flush chamber and said flexible, resilient distal end sealing means is disposed inside said flush chamber adjacent to said circumferential lip.

3. An endoscopic cannulated instrument cleaning apparatus comprising a flush chamber body having a proximal end fitted with a stopper having an aperture therethrough and a distal end fitted with an instrument receiving stopper having an aperture therethrough and an inwardly projecting circumferential lip at said distal end of said flush chamber body, whereby said instrument receiving stopper cannot be removed from said distal end of said flush chamber body.

4. An endoscopic cannulated surgical instrument cleaning apparatus comprising a flushing board having a neck extending from a substantially flat flushing board and including a plurality of spaced parallel yokes fixed to said neck, each said yoke having a U-shaped channel, with said U-shaped channels aligned along a longitudinal center line of said flushing board.

5. An apparatus according to claim 4 further comprising a plurality of fasteners for fixing said yokes to said neck.

6. An apparatus according to claim 4 further comprising a flushing board having a substantially rectangular plan.

7. An endoscopic cannulated surgical instrument cleaning apparatus comprising:
 a. a syringe having a nipple on a distal end;
 b. a flush chamber comprising a flush chamber body having proximal end for attachment to said nipple and means for sealing said nipple relative to said flush chamber, and a distal end, and means for sealing said distal end relative to an endoscopic cannulated instrument to be flushed;

c. said nipple is inserted into said syringe sealing means; and d. a flushing board comprising a neck having a plurality of spaced parallel yokes fixed thereto, each said yoke having a U-shaped channel with said U-shaped channels aligned along a longitudinal center line of said flushing board and said syringe is placed in said yokes.

8. An apparatus according to claim 7 wherein said syringe further includes a handle portion and said handle portion lies adjacent to a proximal side of a proximal yoke of said flushing board.

9. An endoscopic cannulated surgical instrument cleaning apparatus comprising:

a. a syringe having a nipple on a distal end;

b. a flush chamber having a flush chamber body including a proximal end and a distal end, a syringe receiving stopper in a proximal end and an instrument receiving stopper in a distal end and said nipple is inserted into said syringe receiving stopper; and c. a flushing board comprising a neck extending from a flushing board body, said neck having a plurality of spaced parallel yokes fixed thereto, each said yoke having a U-shaped channel with said U-shaped channels aligned along a longitudinal center line of said flushing board and said syringe is placed in said yokes.

10. An apparatus according to claim 9 wherein said syringe further comprises a plunger shaft having a head at a distal end and a thumb support on a proximal end, with said plunger being inserted into a cylindrical body, and said cylindrical body further comprises a nipple and an orifice through said nipple and a bifurcated handle portion and said bifurcated handle portion lies adjacent to a proximal side of a proximal side of a proximal yoke of said flushing board and said syringe body lies in said U-shaped channels.

* * * * *

UNITED STATES PATENT AND TRADEMARK OFFICE
CERTIFICATE OF CORRECTION

PATENT NO. : 5,279,317
DATED : January 18, 1994
INVENTOR(S) : Michael E. Bowman; Michael J. Armentrout; and Drake L. Koch It is certified that error appears in the above-indentified patent and that said Letters Patent is hereby corrected as shown below:

In Claim 1, column 12, lines 25-26 of the Patent, change "distal" to --proximal--.

In Claim 1, column 12, line 27 of the Patent, change "flow" to --flowing--.

Signed and Sealed this

Twenty-ninth Day of August, 1995

Attest:

BRUCE LEHMAN

*Attesting Officer*    *Commissioner of Patents and Trademarks*